United States Patent
Lee et al.

(10) Patent No.: US 9,182,373 B2
(45) Date of Patent: Nov. 10, 2015

(54) APPARATUS AND METHOD FOR DETECTING CRACK IN SMALL-BORE PIPING SYSTEM

(71) Applicant: INDUSTRY-ACADEMIC COOPERATION FOUNDATION CHOSUN UNIVERSITY, Gwangju (KR)

(72) Inventors: Jin Yi Lee, Gwangju (KR); Jong Woo Jun, Gwangju (KR); Jung Min Kim, Gwangju (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 86 days.

(21) Appl. No.: 13/667,064

(22) Filed: Nov. 2, 2012

(65) Prior Publication Data
US 2013/0314082 A1    Nov. 28, 2013

(30) Foreign Application Priority Data
May 22, 2012    (KR) .......................... 10-2012-0054419

(51) Int. Cl.
*G01N 27/82* (2006.01)
*G01V 3/18* (2006.01)
(52) U.S. Cl.
CPC . *G01N 27/82* (2013.01); *G01V 3/18* (2013.01)
(58) Field of Classification Search
CPC ...................................................... G01N 27/82
See application file for complete search history.

(56) References Cited

U.S. PATENT DOCUMENTS

| | | | | |
|---|---|---|---|---|
| 3,597,678 | A * | 8/1971 | Fearon | 324/220 |
| 6,768,299 | B2 * | 7/2004 | Almaguer | 324/221 |
| 2005/0007108 | A1 * | 1/2005 | Dogaru | 324/235 |
| 2010/0042336 | A1 * | 2/2010 | Lee et al. | 702/38 |

OTHER PUBLICATIONS

J. Lee et al., Solid-State Bobbin-Type Hall Sensor Arrays with High Spatial Resolution for Inspecting Cracks in a Small-Bore Piping System, Poster Session ET09 at IEEE International Magnetic Conference 2012, Vancouver, Canada, May 7-11, 2012.
J. W. Jun et al., Solid-State Bobbin-Type Hall Sensor Arrays with High Spatial Resolution for Inspecting Cracks in a Small-Bore Piping System, Proceedings of APCF5-MM 2012, Paper No. 169, pp. 258-259.

(Continued)

*Primary Examiner* — Minh N Tang
(74) *Attorney, Agent, or Firm* — The PL Law Group, PLLC (57) ABSTRACT

Disclosed herein are an apparatus and method for detecting a crack in a small-bore piping system. The apparatus includes a sensor unit, a bobbin coil, a power supply unit, and a signal reception unit. The sensor unit is configured such that a plurality of magnetic sensors is arranged thereon and formed to be cylindrical. The bobbin coil is wound around the outside surface of the sensor unit. The power supply unit applies direct current (DC) power to the sensor unit and alternating current (AC) power to the bobbin coil. The signal reception unit quantifies a signal from the sensor unit. The sensor unit detects the distribution of a magnetic-field attributable to the crack in the small-bore piping system based on the AC power applied to the bobbin coil.

11 Claims, 7 Drawing Sheets

(56) References Cited

OTHER PUBLICATIONS

J Lee et al., Eddy Current Imager Using Bobbin-Type Hall Sensor Arrays for NDE in Small-Bore Piping System, Abstracts: Review of Progress in Quantitative NDE, Denver Colorado, Jul. 15-20, 2012, p. 170.

J Lee et al., 3-D Magnetic Vector Field Camera Using Integrated Hall and MR sensor Arrays, EMSA 2012: 9th European Magnetic Sensors & Actuators Conference: Book of Abstracts, p. 29-30.

J. Lee et al., Bobbin-Type Solid-State Hall Array with High Spatial Resolution for Inspecting Cracks Inspection in Small-Bore Piping Systems, IEEE Transactions on Magnetics, vol. 48, No. 11, p. 3704-3707, Nov. 2012.

J Jun et al., Eddy Current Imager Based on Bobbin-Type Hall Sensor Arrays for Nondestructive Evaluation in Small-Bore Piping System, The 39th Annual Review of Progress in Quantitative Nondestructive Evaluation AIP Conf. Proc. 1511, 502-509 (2013).

* cited by examiner

APPARATUS AND METHOD FOR DETECTING CRACK IN SMALL-BORE PIPING SYSTEM

CROSS REFERENCE TO RELATED APPLICATIONS AND CLAIM OF PRIORITY

This patent application claims priority to Korean Patent Application number 10-2012-0054419, filed on May 22, 2012, entire contents of which are incorporated herein by reference.

BACKGROUND

1. Field of the Invention

The present invention relates generally to an apparatus and method for detecting a crack.

2. Description of the Related Art

If the heat exchangers such as a condenser, conductor and steam generator of a nuclear power plant, the barrel of a gun, an oil pipeline, or the like is damaged because of the corrosion, fatigue or crack of its piping system, a very serious accident may occur. In order to prevent such accidents, apparatuses for detecting a crack in a small-bore piping system, such as an eddy current testing (ECT) apparatus, have been developed.

Conventional apparatuses for detecting a crack in a small-bore piping system chiefly use a pickup coil or a pancake coil.

A detection apparatus using a pickup coil functions to allow the pickup coil to be inserted into a small-bore piping system, apply an alternating current (AC) current to an input coil side, measure a current induced on an output coil side, and then detect a crack. This detection apparatus is disadvantageous in that it is difficult to detect a small crack because the size of its sensor is large, and it is also difficult to estimate the shape or size of a crack.

A detection apparatus using a pancake coil functions to allow a small pancake-type coil to be inserted into a piping system, move the coil in the axial direction of the piping system while rotating the coil, and then measure a change in induced current inside the piping system in two dimensions. While this detection apparatus is advantageous in that it can measure a small crack and measure the shape and size of a crack, it is disadvantageous in that a scanner is required, a long time is required to perform measurement and the size of a sensor is limited.

SUMMARY

Accordingly, one or more embodiments of the present invention has been made keeping in mind the above problems occurring in the prior art, and an aspect of the present invention is to provide an apparatus and a method for detecting a crack in a small-bore piping system, in which in order to measure a crack in a small-bore piping system, magnetic sensors arranged in a cylindrical form and a bobbin coil are combined with each other, thereby achieving improved spatial resolution, improved detection speed, and no need for circular rotation.

An aspect of the present invention provides an apparatus for detecting a crack in a small-bore piping system, the apparatus including a sensor unit including a plurality of magnetic sensors in a matrix and formed to be cylindrical; a bobbin coil wound around the outside surface of the sensor unit; a power supply unit to apply direct current (DC) power to the sensor unit and alternating current (AC) power to the bobbin coil; and a signal reception unit to receive and quantify a signal from the sensor unit; wherein the sensor unit detects a distribution of a magnetic-field attributable to the crack in the small-bore piping system based on the AC power applied to the bobbin coil.

Each of the magnetic sensors may include first and second input terminals to apply the DC power and the ground power, and first and second output terminals to output the detecting signals.

The apparatus may further include a first input switch unit to be switched to apply input power to the first input terminal; and a second input switch unit to be switched to apply ground power to the second input terminal.

The first input switch unit may include a plurality of switching elements whose first ends are connected to the first input terminals of the magnetic sensors arranged in the rows and whose second ends are connected to the power supply unit.

The second input switch unit may include a plurality of switching elements whose first ends are connected to the second input terminals of the magnetic sensors arranged in the rows and whose second ends are connected to the ground power.

The first and second input switch units may be formed in a vertical direction, and each include switching elements whose number is equal to a number of the magnetic sensors formed in the vertical direction.

The apparatus may further include a switch control unit to apply first control signals that sequentially turn the plurality of switching elements of the first input switch unit on and off and to apply second control signals that sequentially turn the plurality of switching elements of the second input switch unit on and off.

In order to accomplish one or more aspects, the present invention provides a method of detecting a crack in a small-bore piping system using a sensor module including a sensor unit having a plurality of magnetic sensors in a matrix and formed to be cylindrical and a bobbin coil wound around an outside surface of the sensor unit, the method including generating a magnetic field attributable to induced current in the small-bore piping system by applying AC current to the bobbin coil while moving the sensor unit in an axial direction of the small-bore piping system, and activating magnetic sensors of a plurality of magnetic sensors of the sensor unit arranged in at least any one row; detecting a change in the magnetic field in the small-bore piping system using the sensor unit; and locating the sensor unit in an area in which the change in the magnetic field is detected, and measuring a distribution of the magnetic field using the sensor unit.

The locating and measuring may include sequentially turning switching elements of a first input switch unit connected in common to first input terminals of Hall sensors arranged in rows in the sensor unit on and off; and sequentially turning switching elements of a second input switch unit connected in common to second input terminals of the sensor unit on and off in synchronization with the first input switch unit.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

The present invention is not limited to specific embodiments, but may be subject to a variety of modifications and additions and have a variety of embodiments. Furthermore, it should be appreciated that the present invention includes all modifications, equivalents, and replacements that pertain to the technical scope and spirit of the present.

Although the terms "first," "second," "third," etc. may be used herein to describe various elements and/or components, these elements and/or components should not be limited by these terms. These terms may be only used to distinguish one element and/or component from another element and/or component.

Throughout the overall specification, the same reference numerals are used to designate the same or similar components.

Unless the context otherwise clearly indicates, terms used in the singular include the plural. Furthermore, it should be appreciated that the terms "comprise," "include," and "have" are intended to specify the presence of features, numbers, steps, operations, components, parts, or combinations thereof, but it should not be appreciated that the terms are not intended to exclude the presence of or the possibility of addition of one or more features, numbers, steps, operations, components, parts, or combinations thereof.

Embodiments of the present invention will be described in detail below with reference to FIGS. 1 to 10.

Figure 1:
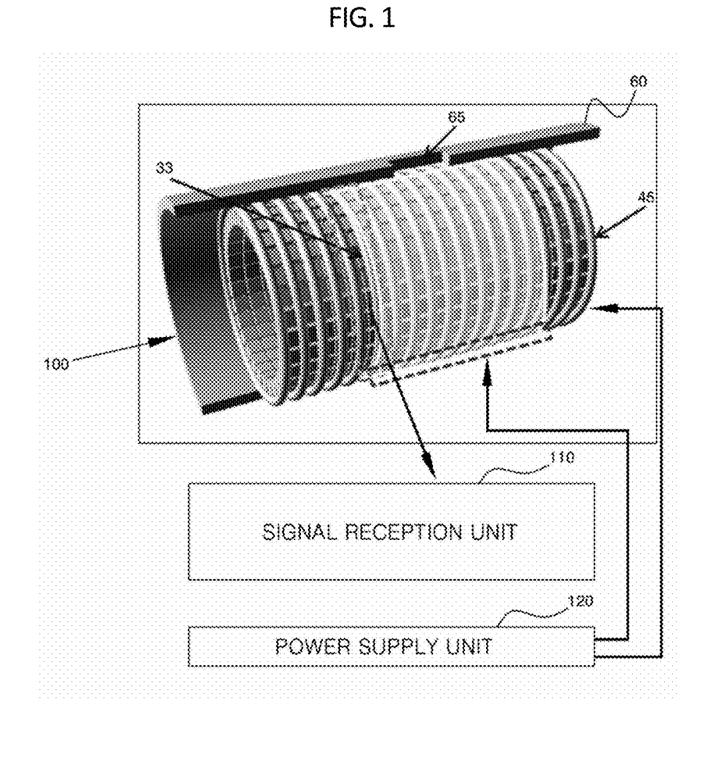
FIG. 1 is a block diagram showing an apparatus for detecting a crack in a small-bore piping system according to an embodiment of the present invention.
Figure 2:
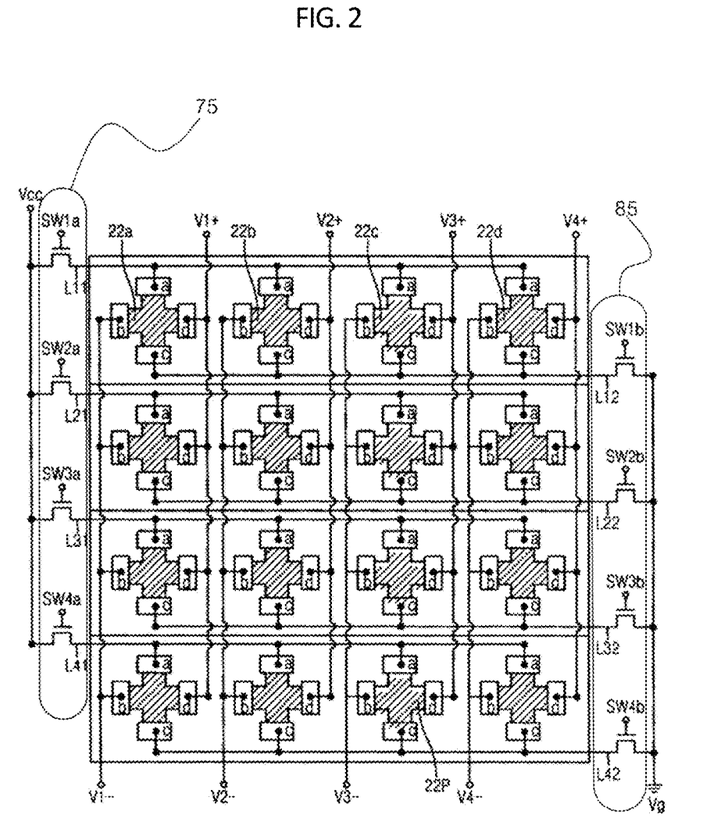
FIG. 2 is a circuit diagram showing the sensor unit of FIG. 1.
Figure 3:
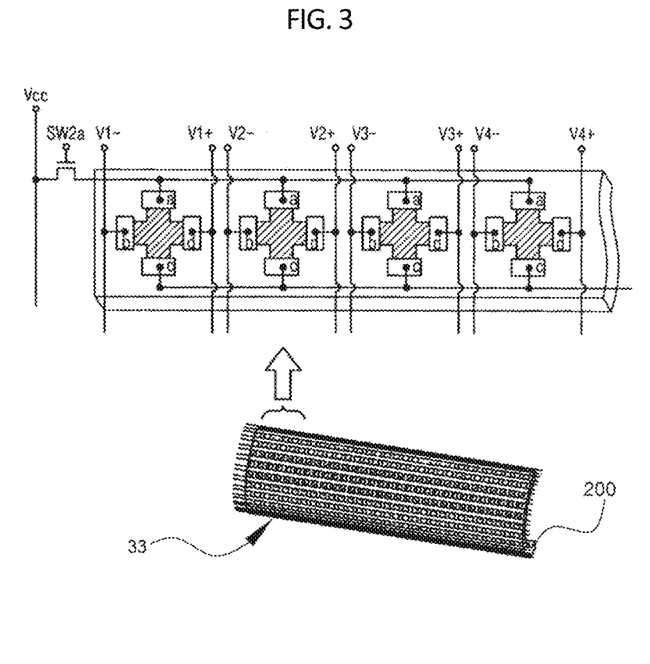
FIG. 3 is a diagram showing that the sensors of each of the sensor units of FIGS. 1 and 2 can be arranged on a single curved surface.
Figure 4:
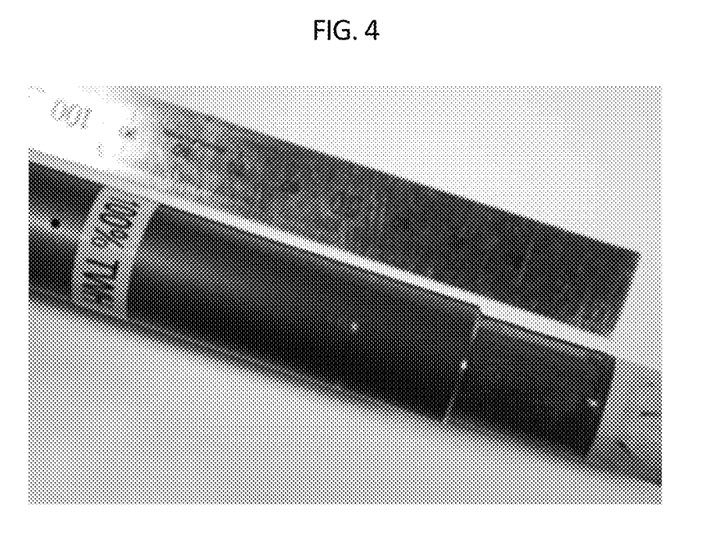
FIG. 4 is a photograph showing a sensor module manufactured according to an embodiment of the present invention.

FIG. 1 is a block diagram showing an apparatus for detecting a crack in a small-bore piping system according to an embodiment of the present invention, FIG. 2 is a circuit diagram showing the sensor unit of FIG. 1, FIG. 3 is a diagram showing that the sensors of each of the sensor units of FIGS. 1 and 2 can be arranged on a single curved surface, and FIG. 4 is a photograph showing a sensor module manufactured according to an embodiment of the present invention. Here, the sensor module shown in the photograph of FIG. 4 is manufactured by winding a bobbin coil around the outside surface of the sensor unit of FIG. 3.

Referring to FIGS. 1 to 4, the apparatus for detecting a crack in a small-bore piping system according to this embodiment of the present invention may include a sensor module 100, a power supply unit 120, and a signal reception unit 110. Small-bore pipe includes piping which is one inch and smaller in diameter.

More specifically, the power supply unit 120 may supply DC power and AC power to a sensor module 100. The DC power VCC is supplied to a sensor unit 33, while the AC power is supplied to a bobbin coil 45.

The signal reception unit 110 may receive a signal from the sensor unit 33, and process the signal so that the form of a crack in a crack region can be visualized.

For example, the signal reception unit 110 may include an amplification unit, a filter unit, and a signal conversion unit. The amplification unit may amplify the signal received from the sensor unit 33. The filter unit may eliminate noise from the amplified signal. The signal conversion unit may convert the noise-free signal into a digital signal so that the noise-free signal can be displayed on the monitor of a computer.

The sensor module 100 may include the sensor unit 33 and the bobbin coil 45, as described above. The sensor module 100 may be formed to have a diameter that is smaller than that of the small-bore piping system 60.

The sensor module 100 may detect a crack 65 in a small-bore piping system 60 by measuring the distribution of a magnetic field using magnetic sensors arranged in the sensor unit 33 in the form of a matrix. The sensor unit 33 may include Hall sensors, as an example of magnetic sensors. However, such as magneto-resistive (MR) sensor, a giant magneto-resistive (GMR) sensor, a giant magneto-impedance (GMI) sensor, a spin dependent tunneling (SDT) sensor, and a magnetic tunnel junction (MTJ) sensor, and etc. may be used as the magnetic sensors of the sensor unit 33, besides Hall sensors.

The sensor module 100 may generate an induced current in the small-bore piping system using the AC current applied to the bobbin coil 45, and measure the distribution of a magnetic field attributable to the induced current of the small-bore piping system using the sensor unit 33.

The sensor module 100 may first operate Hall sensors arranged in at least one row in order to search for the location of a crack in the small-bore piping system. That is, the Hall sensors arranged in the row measure a magnetic field while moving along the inside of the small-bore piping system. In this case, it may be determined that a crack is present in a region in which a change in the magnetic field occurs.

Thereafter, the size and state of the crack may be measured by placing the sensor module 100 at a location at which the crack occurred, operating all the Hall sensors of the sensor unit 33 and then measuring the distribution of the magnetic field.

The sensor unit 33 may include Hall sensors 22a to 22d that are arranged on a board 200 in M (a natural number) rows and in N (a natural number) columns.

M power lines L11 to L41 for supplying power, M ground lines L12 to L42, N first output lines V1+ to V4+ for outputting positive voltages, N second output lines V1− to V4− for outputting negative voltages, a first input switch unit 75, and a second input switch unit 85 are implemented on the board 200.

The VCC terminals "a" of the sensors included in the M-th row are connected to the power line for the M-th row.

The ground terminals "c" of the sensors in the M-th row are connected to a ground line for the M-th row.

The first output terminals "d" of the sensors included in the N-th row are connected to the first output line VN+ for the N-th row.

The second output terminals "b" of the sensors included in the N-th row are connected to the second output line VN− for the N-th row.

The first input switch unit 75 may include a plurality of switches connected to the power lines L11 to L41, respectively, and selectively provide an input voltage to the power lines L11 to L41. For example, when the switch SWa1 of the first input switch unit 75 is turned on, input power VCC is applied to the power line L11 for the first row. When the switch SWa4 is turned on, input power is applied to the power line L14 for the fourth row. Here, the switches SWa1 to SWa4 may be sequentially turned on and off. That is, when the switch SWa1 is turned on, the remaining switches SWa2 to SWa4 are turned off. In contrast, when the switch SWa2 is turned on, the remaining switches SWa1, SWa3, and SWa4 are turned off.

The second input switch unit 85 may include a plurality of switches connected to ground lines L12 to L42, respectively, and selectively provide ground power GND to the ground lines L12 to L42. For example, when the switch SWb1 of the second input switch unit 85 is turned on, the ground power GND is applied to the ground line L12 for the first row. When the switch SWb4 is turned on, the ground power GND is applied to the ground line L42 for the fourth row. Here, the switches SWb1 to Swb4 may be sequentially turned on and off. That is, when the switch SWb1 is turned on, the remaining switches SWb2 to SWb4 are turned off. In contrast, when the switch SWb2 is turned on, the remaining switches SWb1, SWb3, and SWb4 are turned off.

Meanwhile, according to an embodiment of the present invention, as soon as the switches of the first input switch unit 75 are turned on, the switches of the second input switch unit 85 may be simultaneously turned on in synchronization with the turning on of the switches of the first input switch unit 75. For example, when the switch SWa1 is turned on, the switch SWb1 may be turned on at the same time. Subsequently, when the switch SWa2 is turned on, the switch SWb2 may be turned on.

Accordingly, both the input power VCC and the ground power GND may be provided to the sensors arranged in each row in a batch manner. Therefore, the distribution of the magnetic field can be measured at regular intervals without requiring a scanner.

FIG. 3 is a diagram showing the sensor unit of FIG. 2 formed on the board 200. The board 200 is a flexible board 200. The above-described sensors 22a to 22d are arranged on the cylindrical surface of the board 200.

The bobbin coil 45 supplies an AC current, and generates an induced current in the small-bore piping system 60. In this case, when a crack 65 is present in the small-bore piping system 60, the location, size and state of the crack 65 can be detected by measuring the distortion of the induced current generated by the crack 65 and the intensity of a magnetic field influenced by the distortion of the induced current using the above-described sensor unit 33.

As described above, in the sensor module according to the embodiment of the present invention, when an AC current is applied to the bobbin coil 45, in which case an induced current may be generated in the small-bore piping system. Here, when a crack is present in the small-bore piping system, the induced current is changed, and thus an induced magnetic field may be generated, as shown in FIG. 5.

Figure 5:
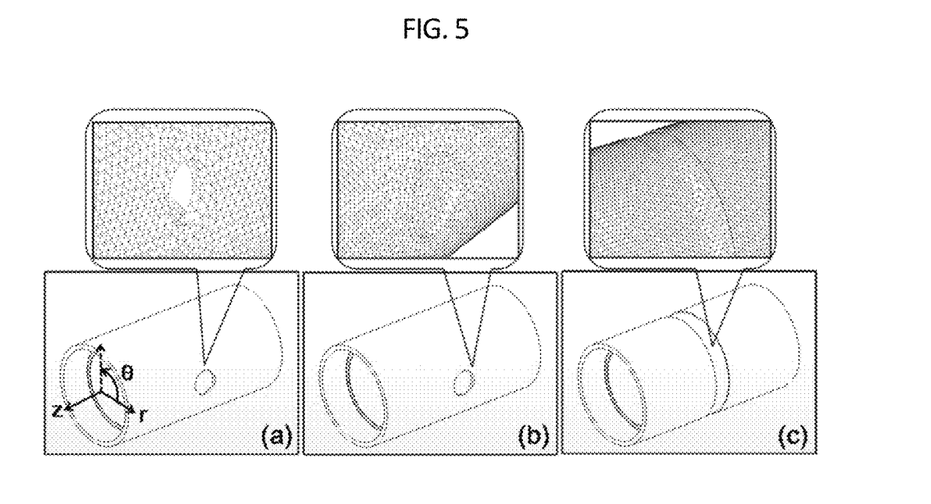
FIG. 5 is a diagram showing a model that is used to analyze the distribution of an electromagnetic field when a bobbin coil is inserted into a piping system having Outside Diameter Stress Corrosion Cracking (ODSCC)

FIG. 5 is a diagram showing a model that is used to analyze the distribution of an electromagnetic field when a bobbin coil is inserted into a piping system having ODSCC.

In FIG. 5, r, θ and z represent the radial, circumferential, and axial directions, respectively, in a cylindrical coordinate system. It was assumed that the inner diameter and thickness of the piping system were 17.28 mm and 0.89 mm, respectively, the material thereof was titanium having a conductivity of $5.2 \times 10^{-7}$, and the size of a sensing area was 0.78 mm. A three-dimensional numerical analysis was carried out by a finite element method (FEM) using commercial software, that is, ANSYS Ver. 11.0 SP1 UP20070830 EMAG. It was also assumed that the diameter and length of a bobbin coil were 0.2 mm and 35 mm, respectively, and an AC current of 0.6 A was applied to the bobbin coil at 5 kHz. ODSCC was modeled as hole- and circumference-types, as shown in Table 1. It was assumed that the hole-type ODSCC had a diameter in the range of 1.5 to 4.6 mm and a depth in the range of 37 to 100% (see FIG. 5 (b)). It was assumed that the circumference-type ODSCC had a width of 3 mm and a depth of 19% (see FIG. 5 (c)). The distribution of an electromagnetic field was computed on a measuring surface, that is, the θ-z plane, at a diameter of 16 mm, i.e., r=8 mm, inside of the bobbin coil.

TABLE 1

| No. | Shape | Depth | Width | Surface area | Volume |
|---|---|---|---|---|---|
| 1 | hole-type | 0.860 mm | 1.5 mm | 1.77 mm² | 1.52 mm³ |
| 2 | | 0.697 mm | 1.8 mm | 2.54 mm² | 1.77 mm³ |
| 3 | | 0.499 mm | 2.7 mm | 5.73 mm² | 2.86 mm³ |
| 4 | | 0.335 mm | 4.6 mm | 16.62 mm² | 5.57 mm³ |
| 5 | | 0.315 mm | 4.6 mm | 16.62 mm² | 5.29 mm³ |
| 6 | circumferential-type | 0.163 mm | 3.0 mm | 104.57 mm² | 17.09 mm³ |

Figure 6:
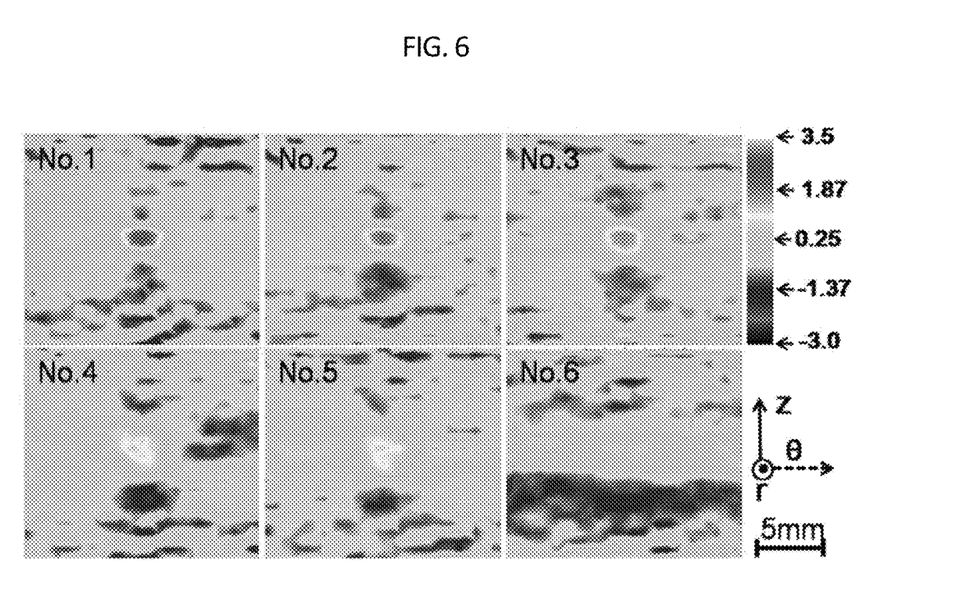
FIG. 6 shows the results of the analysis of an electromagnetic field distorted by ODSCC.

FIG. 6 shows the results of the analysis of the electromagnetic field distorted by ODSCC. Assuming that Br is the r-directional magnetic field on the θ-z plane, FIG. 6 shows the size of ΔBr passing through the center of ODSCC on the measuring surface, which is represented by the following Equation 1:

$$\Delta Br(\theta,z) = Br(i+1,j) - Br(i,j) \quad (1)$$

(ΔBr represents the differences between Br(i,j) and the neighbor Br(i+1,j))

Image No. 1 of FIG. 6 provides the clearest image in spite of the smallest width of a crack. Furthermore, comparing Image Nos. 1 and 4 of FIG. 6, when the area of ODSCC is wide, the distortion of an electromagnetic field around a crack is widely distributed. Meanwhile, comparing Image Nos. 4 and 5 of FIG. 6, it can be noted that when the depth of a crack is small, as shown in image No. 5 of FIG. 6, a crack indication signal decreases in spite of the same area. It can be noted that, although the direction of application of current induced by the bobbin coil is identical to the longitudinal direction of circumferential ODSCC, as shown in image No. 6 of FIG. 6, the distortion of an electromagnetic field is generated.

Figure 7:
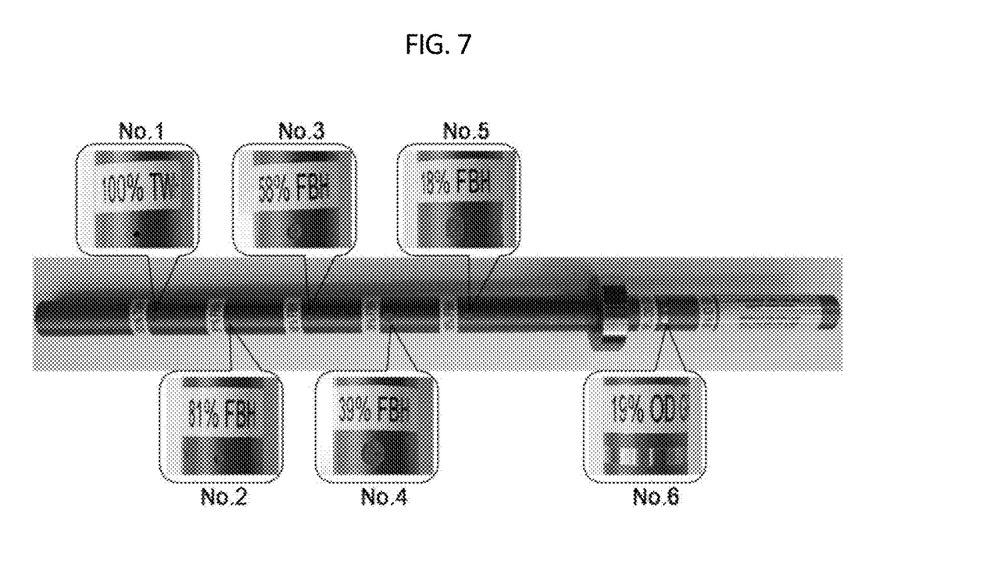
FIG. 7 shows an apparatus for verifying whether the apparatus for detecting a crack according to the embodiment of the present invention has detected ODSCC.
Figure 8:
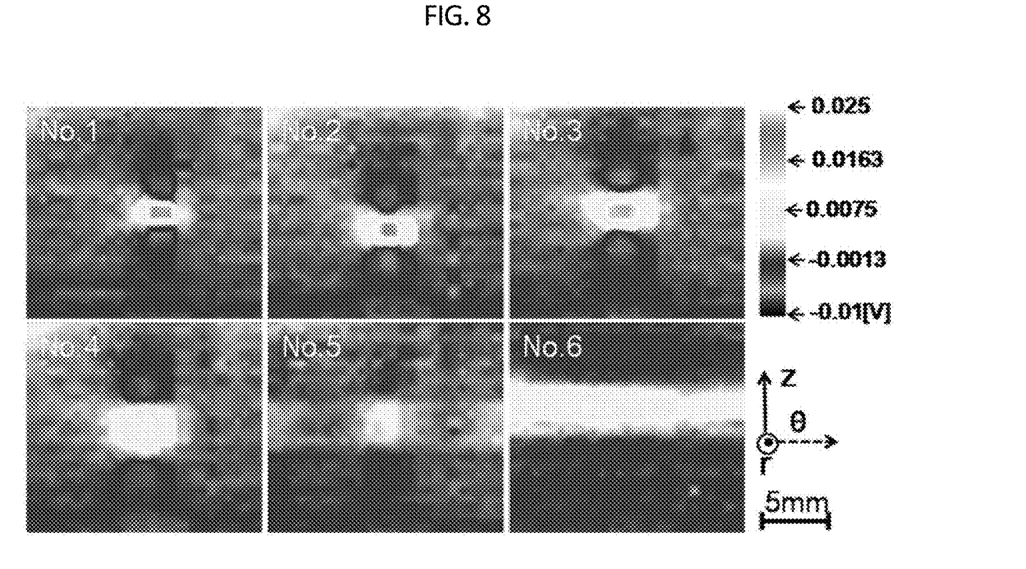
FIG. 8 shows the results of the detection of ODSCC.
Figure 9:
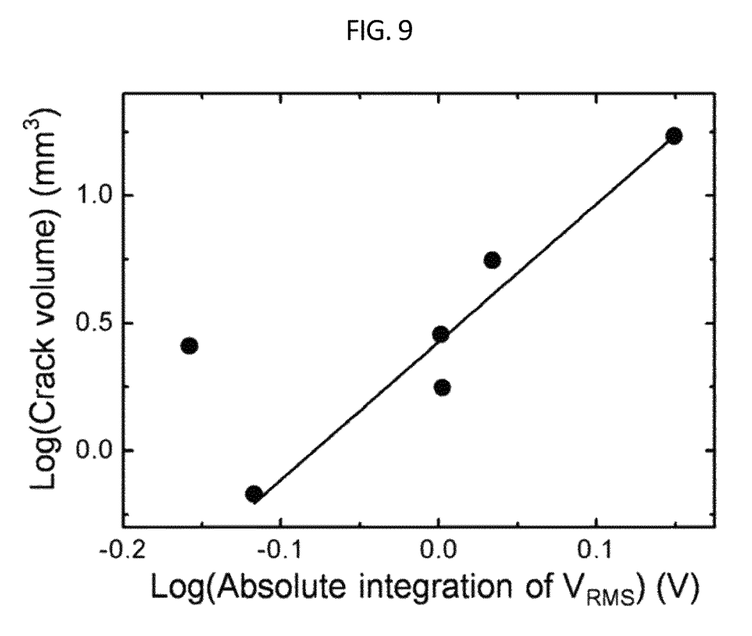
FIG. 9 is a graph showing the relationship between the volume of ODSCC and the sum of $V_{RMS}$.

FIG. 7 shows an apparatus for verifying whether the apparatus for detecting a crack according to the embodiment of the present invention has detected ODSCC, FIG. 8 shows the results of the detection of ODSCC, and FIG. 9 is a graph showing the relationship between the volume of ODSCC and the sum of $V_{RMS}$.

Referring to FIGS. 7 to 9, in the experiment of the embodiment of the present invention, a piping system made of titanium alloy, that is, ASME SB338 GR2, was used. The inner diameter and thickness of the piping system were 17.28 mm and 0.86 mm, respectively. Here, the hall-type ODSCC had a diameter in the range from 1 to 4.6 mm and a depth in the range from 18 to 100%. Furthermore, the circumference-type DSCC had a width of 3 mm and a depth of 19%.

Table 2 shows the results of the measurement of an electromagnetic field distorted by each ODSCC in a small-bore piping system.

TABLE 2

| No. | Shape | Depth | Width | Surface area | Volume |
|---|---|---|---|---|---|
| 1 | hole-type | 0.860 mm | 1.0 mm | 0.79 mm$^2$ | 0.68 mm$^3$ |
| 2 | | 0.697 mm | 1.8 mm | 2.54 mm$^2$ | 1.77 mm$^3$ |
| 3 | | 0.499 mm | 2.7 mm | 5.73 mm$^2$ | 2.86 mm$^3$ |
| 4 | | 0.335 mm | 4.6 mm | 16.62 mm$^2$ | 5.57 mm$^3$ |
| 5 | | 0.155 mm | 4.6 mm | 16.62 mm$^2$ | 2.57 mm$^3$ |
| 6 | circumferential-type | 0.163 mm | 3.0 mm | 104.57 mm$^2$ | 17.09 mm$^3$ |

Here, the sensor unit 33 having the same circuits as the sensor units 33 of FIGS. 1 to 3 is configured such that 32×32 Hall sensors are arranged along a circumferential surface having an outer diameter of 15 mm at intervals of 0.78 mm. Accordingly, the distribution of an AC magnetic field in an area of 214°×24.96 mm on the O-z plane can be measured.

Here, the amplification ratio of the amplification unit was 17.57 dB. Meanwhile, the bobbin coil 45 formed on the outer wall of the sensor unit 33 had a diameter of 0.2 mm and was wound 140 times. The bobbin coil 45 had an outer diameter of 15.4 mm and a lift-off of 1.2 mm.

An AC current of 600 mA was applied to the bobbin coil 45 at 5 kHz. The amplification unit and the filter unit circuit were implemented using INA128 and AD637JRZ. An analog-digital conversion unit performed digital conversion using NI company's 6071E equipment. As a result of the switching of a power unit at intervals of 30 ms, a magnetic field could be imaged using 32×32 Hall sensors at a speed of about 1 frame/sec.

When a signal obtained by converting a Hall voltage using RMS circuits is referred to as $V_{i,s}$, the difference between the distributions of the magnetic field distribution that are neighboring each in the z-axis direction can be expressed by Equation 2:

$$\Delta V_{RMS}(\theta,z) = V_{RMS}(i+1,j) - V_{RMS}(i,j) \qquad (2)$$

FIG. 8 shows $\Delta_{RMS}$ images that were obtained by the above-described signal reception unit 110 of FIG. 1. From FIG. 8, it can be noted that the results of the experiment are the same as those of the above-described numerical analysis. That is, Image No. 1 of FIG. 8 provides the clearest image in spite of the smallest width of a crack. Furthermore, when the area of ODSCC is wide, the distortion of an electromagnetic field around a crack is widely distributed. Meanwhile, comparing Image Nos. 4 and 5 of FIG. 8, it can be noted that when the depth of a crack is small, as shown in Image No. 5 of FIG. 8, a crack indication signal decreases in spite of the same area. It can be noted that, although the direction of application of current induced by the bobbin coil is identical to the longitudinal direction of circumferential ODSCC as shown in Image No. 6 of FIG. 8, the distortion of the electromagnetic field can be visualized.

FIG. 9 shows the relationship between the volume of ODSCC(VODSCC) and $\Sigma V_{RMS}$ given by the following expression.

To evaluate the volume of ODSCC, the absolute integration of the magnetic image ($\Sigma V_{RSM}$), given in equation 3 was considered.

$$\sum V_{RMS} = \sum_{j=1}^{n} \sum_{i=1}^{m} |\Delta V_{RMS}(i,j)| \qquad (3)$$

In the above equation i and j represent the point of the pixel in the θ- and z-direction, respectively.

Figure 10:
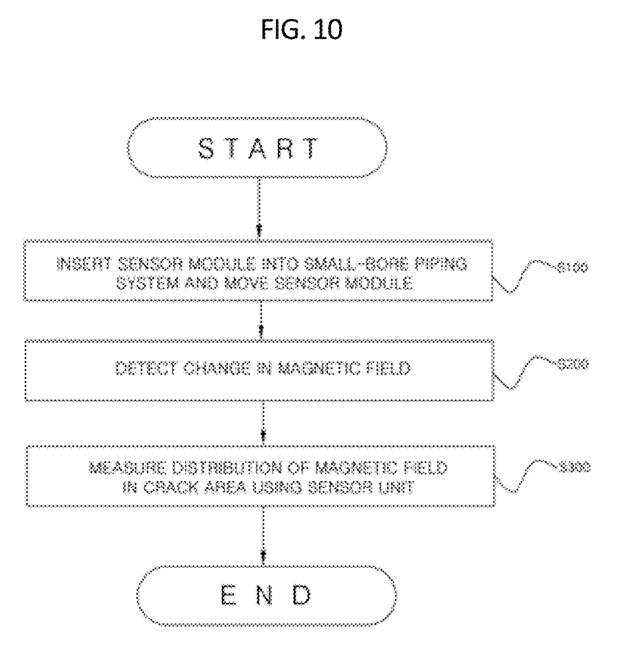
FIG. 10 is a flowchart sequentially showing a method of detecting a crack in a small-bore piping system according to an embodiment of the present invention.

FIG. 10 is a flowchart sequentially showing a method of detecting a crack in a small-bore piping system according to an embodiment of the present invention. FIG. 10 shows the method using one of the sensor modules of FIGS. 1 to 4, and will be described in conjunction with FIGS. 1 to 4 below.

Referring to FIG. 10, the method of detecting a crack in a small-bore piping system according to the embodiment of the present invention may include applying power to the sensor module and moving the sensor unit through the inside of a small-bore piping system in the axial direction thereof (S100), detecting a change in an internal magnetic field through the small-bore piping system (S200), and measuring the distribution of the magnetic field in the region of the small-bore piping system in which there is a crack (S300).

More specifically, the sensor module 100 is inserted into the inside of the small-bore piping system 60. Thereafter, an AC current is applied to the bobbin coil 45, and DC power is applied to the sensor unit 33. In this case, a plurality of Hall sensors arranged in the row direction is activated by turning on any one of a plurality of switching elements provided in the first input switch unit 75 of the sensor unit 33 and any one of a plurality of switching elements provided in the second input switch unit 85. For example, the Hall sensors arranged in the third row are activated by turning on the switch SWa3 and switch SWb3 of the FIG. 2. In this state, the sensor module 100 is moved through the inside of the small-bore piping system 60 in the axial direction thereof at step S100.

Thereafter, a magnetic field in the small-bore piping system 60 is detected by the sensor module 100 that moves through the inside of the small-bore piping system 60 in the axial direction thereof (S200). In this case, it may be estimated that there is the crack 65 in a region in which there is a change in the magnetic field.

Thereafter, the sensor module 100 is located in the region in which there is the change in the magnetic field and then the distribution of the magnetic field is measured (S300). A method of measuring the distribution of the magnetic field may be configured to receive signals from the Hall sensors while sequentially turning the first and second input switch units 75 and 85 on and off and quantify the signals, thereby visualizing the distribution of the magnetic field.

As described above, the apparatus and method for detecting a crack in a small-bore piping system according to the embodiments of the present invention can precisely inspect a small-bore piping system using the sensor unit in which the magnetic sensors are arranged on the circumferential surface and the sensor module in which the bobbin coil is wound around the circumferential surface of the sensor unit. The apparatus and method for detecting a crack in a small-bore piping system according to the present invention can improve spatial resolution and can rapidly detect a crack in a piping system.

Although the embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. An apparatus for detecting a crack in a small bore piping system, the apparatus comprising:
   a sensor unit comprising a plurality of magnetic sensors in a matrix and formed to be cylindrical;
   a bobbin coil wound around an outside surface of the sensor unit;

a power supply unit to apply direct current (DC) power to the sensor unit and alternating current (AC) power to the bobbin coil; and a signal reception unit to receive and quantify a signal from the sensor unit;

wherein the sensor unit detects a distribution of a magnetic field attributable to the crack in the small bore piping system based on the AC power applied to the bobbin coil.

2. The apparatus of claim 1, wherein each of the magnetic sensors comprises a first input terminal to apply the DC power, a second input terminal to apply the ground power, and a first output terminal and a second output terminal to output the detecting signals.

3. The apparatus of claim 2, further comprising:
a first input switch unit to be switched to apply direct current (DC) power to the first input terminal; and
a second input switch unit to be switched to apply ground power to the second input terminal.

4. The apparatus of claim 3, wherein the first input switch unit comprises a plurality of switching elements whose first ends are connected to the first input terminals of the magnetic sensors arranged in the rows and whose second ends are connected to the power supply unit.

5. The apparatus of claim 3, wherein the second input switch unit comprises a plurality of switching elements whose first ends are connected to the second input terminals of the magnetic sensors arranged in the rows and whose second ends are connected to the ground power.

6. The apparatus of claim 3, wherein the first and second input switch units are formed in a vertical direction, and each comprise switching elements whose number is equal to a number of the magnetic sensors formed in the vertical direction.

7. The apparatus of claim 3, further comprising a switch control unit to apply first control signals that sequentially turn the plurality of switching elements of the first input switch unit on and off, and to apply second control signals that sequentially turn the plurality of switching elements of the second input switch unit on and off.

8. The apparatus of claim 1, wherein the plurality of magnetic sensors are a plurality of Hall sensors.

9. The apparatus of claim 1, wherein the plurality of magnetic sensors are a plurality of one selected from the group consisting of a magneto-resistive (MR) sensor, a giant magneto-resistive (GMR) sensor, a giant magneto-impedance (GMI) sensor, a spin dependent tunneling (SDT) sensor, and a magnetic tunnel junction (MTJ) sensor.

10. A method of detecting a crack in a small-bore piping system using a sensor module including a sensor unit comprised of a plurality of magnetic sensors in a matrix and formed to be cylindrical and a bobbin coil wound around an outside surface of the sensor unit, the method comprising:
generating a magnetic field attributable to induced current in the small-bore piping system by applying AC current to the bobbin coil while moving the sensor unit in an axial direction of the small-bore piping system, and activating the magnetic sensors arranged in at least one row;
detecting a change in the magnetic field in the small-bore piping system using the sensor unit; and
locating the sensor unit in an area in which the change in the magnetic field is detected, and measuring a distribution of the magnetic field using the sensor unit.

11. The method of claim 10, wherein the locating and measuring comprises:
sequentially turning switching elements of a first input switch unit connected in common to first input terminals of the magnetic sensors arranged in rows in the sensor unit on and off; and
sequentially turning switching elements of a second input switch unit connected in common to second input terminals of the magnetic sensors arranged in the rows in sensor unit on and off in synchronization with the first input switch unit.

\* \* \* \* \*